United States Patent
Bae et al.

(10) Patent No.: US 11,730,417 B2
(45) Date of Patent: Aug. 22, 2023

(54) APPARATUS AND METHOD FOR DETECTING R PEAK OF ECG SIGNAL USING ADAPTIVE MEDIAN FILTER

(71) Applicant: Electronics and Telecommunications Research Institute, Daejeon (KR)

(72) Inventors: Tae Wuk Bae, Daejeon (KR); Kee Koo Kwon, Daejeon (KR); Kyu Hyung Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 168 days.

(21) Appl. No.: 17/475,913

(22) Filed: Sep. 15, 2021

(65) Prior Publication Data

US 2022/0095981 A1    Mar. 31, 2022

(30) Foreign Application Priority Data

Sep. 28, 2020  (KR) .......................... 10-2020-0126305

(51) Int. Cl.
*A61B 5/352*  (2021.01)
*A61B 5/00*   (2006.01)

(52) U.S. Cl.
CPC .............. *A61B 5/352* (2021.01); *A61B 5/725* (2013.01)

(58) Field of Classification Search
None
See application file for complete search history.

(56) References Cited

U.S. PATENT DOCUMENTS

| | | | |
|---|---|---|---|
| 2010/0049059 | A1 | 2/2010 | Ha et al. |
| 2014/0100465 | A1* | 4/2014 | Kim ........................ A61B 5/318 |
| | | | 600/509 |
| 2015/0105679 | A1 | 4/2015 | Hwang |
| 2016/0045117 | A1* | 2/2016 | Liu ..................... A61B 5/02405 |
| | | | 600/502 |

FOREIGN PATENT DOCUMENTS

| | | |
|---|---|---|
| KR | 10-2012-0133790 | 12/2012 |
| KR | 10-2014-0041327 | 4/2014 |
| KR | 10-1524596 | 6/2015 |
| KR | 10-2020-0024518 | 3/2020 |

* cited by examiner

*Primary Examiner* — Ankit D Tejani
(74) *Attorney, Agent, or Firm* — Kile Park Reed & Houtteman PLLC

(57) ABSTRACT

Provided is a method of detecting the R peak of an electrocardiogram (ECG) signal using an adaptive median filter. The method includes allowing an ECG signal (hereinafter, referred to as a first ECG signal) received from an ECG signal measuring apparatus having a predetermined sampling rate to pass through an adaptive median filter, calculating a difference value between the first ECG signal and a signal (hereinafter, referred to as a second ECG signal) passing through the adaptive median filter, extracting R peak candidate groups by applying a maximum filtering size and an adaptive threshold applicable in the adaptive median filter to the calculated difference value between the first and second ECG signals, and detecting an R peak candidate group having a maximum value among the R peak candidate groups as an R peak.

18 Claims, 18 Drawing Sheets

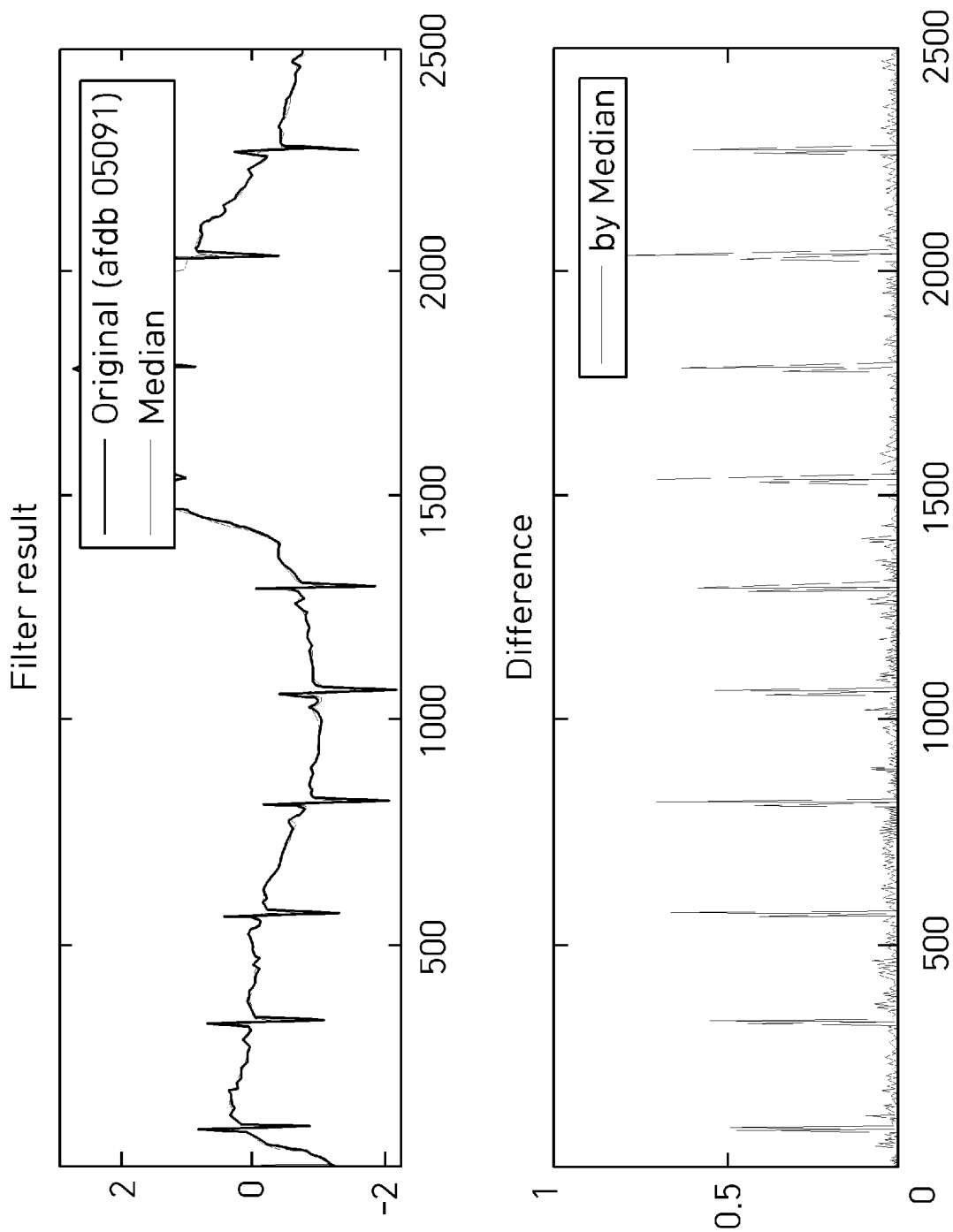

FIG. 8

```
Fs = 250;   % Sampling rate, 360 for Physionet database
Tp = 6;   % Particle time=6 sec
NSB = 3;   % Number of sliding window for 1 minute
N_Tp = 4;   % Number of particle time in sliding window
SS = round(Tp*(N_Tp-1)*Fs);   % Step size of sliding window
TS = Tp*N_Tp*Fs;   % Time of sliding window
N =1;   % Count of sliding window Function Arrhymia_Detection(Stream)
    For each sliding window in stream do
        R(t) : detected R peak in sliding window
        For k = R(1) : R(k)
            Detect Q onset, S offset, P peak, and T peak for R(t)
            Calculate QRS width for R(t)
            Decide whether current beat is Normal or PVC (premature ventricular contraction) or Ischemia or Asystole
        End If N <= NSB   % Less than 1 minute
            Concatenate detected Q onset, S offset, P peak, and T peak
        End If N == NSB   % for 1 minute
            Calculate AA, RR, HR, TRI, TINN, SD1, SD2, OSC % Atrial activity, RR interval, heartrate, triangular index, triangular interpolation of NN histogram, sd1, sd2, oscillation degree
            Decide whether ECG signal of 1 minute is Bigeminy, Trigeminy, Atrial fibrillation, Ventricular tachycardia, Supraventricular tachycardia
            N = 1;
        Else
            N = N + 1;
End     End
```

APPARATUS AND METHOD FOR DETECTING R PEAK OF ECG SIGNAL USING ADAPTIVE MEDIAN FILTER

CROSS-REFERENCE TO RELATED APPLICATION(S)

This application claims priority to and the benefit of Korean Patent Application No. 10-2020-0126305, filed on Sep. 28, 2020, the disclosure of which is incorporated herein by reference in its entirety.

BACKGROUND

1. Field of the Invention

The present invention relates to an apparatus and method for detecting an R peak of an electrocardiogram (ECG) signal using an adaptive median filter considering a sampling rate.

2. Discussion of Related Art

The heart consists of left and right atria and left and right ventricles and contracts and relaxes due to electrical stimulation of the heart muscles. In this case, there may be a case in which regular contraction and relaxation cannot be achieved when electrical stimulation is not generated in the heart so that the electrical stimulation is not transmitted or when abnormally rapid electrical stimulation is generated. Such a case is referred to as cardiac arrhythmia.

In order to detect cardiac arrhythmia, it is essential to detect R peaks from electrocardiogram (ECG) signals.

However, in the conventional methods of detecting R peaks, the R peaks are analyzed and detected based on ECG signals measured using various ECG measuring apparatuses, but the ECG measuring apparatuses are set to have different sampling rates, and thus it is difficult to detect the R peaks.

SUMMARY OF THE INVENTION

The present invention is directed to providing an apparatus and method for detecting an R peak of an electrocardiogram (ECG) signal using an adaptive median filter that is directly applicable to ECG measuring apparatuses having different sampling rates by allowing a filtering size to be adaptively changed according to the sampling rate of the ECG measuring apparatus.

However, the scope of the present invention is not limited to the above-described object and other objects may be present.

According to an aspect of the present invention, there is provided a method of detecting an R peak of an ECG signal using an adaptive median filter. The method includes an ECG signal (hereinafter, referred to as a first ECG signal) received from an ECG signal measuring apparatus having a predetermined sampling rate to pass through an adaptive median filter, calculating a difference value between the first ECG signal and a signal (hereinafter, referred to as a second ECG signal) passing through the adaptive median filter, extracting R peak candidate groups by applying a maximum filtering size and an adaptive threshold applicable in the adaptive median filter to the calculated difference value between the first and second ECG signals, and detecting an R peak candidate group having a maximum value among the R peak candidate groups as an R peak.

According to another aspect of the present invention, there is provided an apparatus for detecting an R peak of an ECG signal using an adaptive median filter. The apparatus includes a sensor unit configured to detect an ECG signal (hereinafter, referred to as a first ECG signal) having a predetermined sampling rate, a memory configured to store a program for detecting an R peak from the first ECG signal using the adaptive median filter, and a processor configured to execute the program stored in the memory. In this case, the processor executes the program to calculate a difference value between the first ECG signal and a signal (hereinafter, referred to as a second ECG signal) obtained by allowing the first ECG signal to pass through the adaptive median filter, extract R peak candidate groups by applying a maximum filtering size and an adaptive threshold applicable in the adaptive median filter to the calculated difference value between the first and second ECG signals, and detect an R peak candidate group having a maximum value among the R peak candidate groups as an R peak.

According to still another aspect of the present invention, there is provided an apparatus for detecting an R peak of an ECG signal using an adaptive median filter. The apparatus includes a communication module configured to receive a measured ECG signal (hereinafter, referred to as a first ECG signal) from an ECG signal measuring apparatus having a predetermined sampling rate, a memory configured to store a program for detecting an R peak from the first ECG signal using the adaptive median filter so that a filtering size is set to correspond to the sampling rate, and a processor configured to execute the program stored in the memory. In this case, the processor executes the program to calculate a difference value between the first ECG signal and a signal (hereinafter, referred to as a second ECG signal) obtained by allowing the first ECG signal to pass through the adaptive median filter, extract R peak candidate groups by applying a maximum filtering size and an adaptive threshold applicable in the adaptive median filter to the calculated difference value between the first and second ECG signals, and detect an R peak candidate group having a maximum value among the R peak candidate groups as an R peak.

In addition, another method of implementing the present invention, another system, and a computer-readable recording medium for recording a computer program for executing the method may be further provided.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIGS. 3A and 3B illustrate graphs showing filtering results and difference values of first ECG signals using a general median filter and an adaptive median filter according to the present invention;

FIG. 8 is a diagram illustrating an example of R peak detection pseudo codes applied to an embodiment of the present invention;

DETAILED DESCRIPTION OF EXEMPLARY EMBODIMENTS

Figure 1:
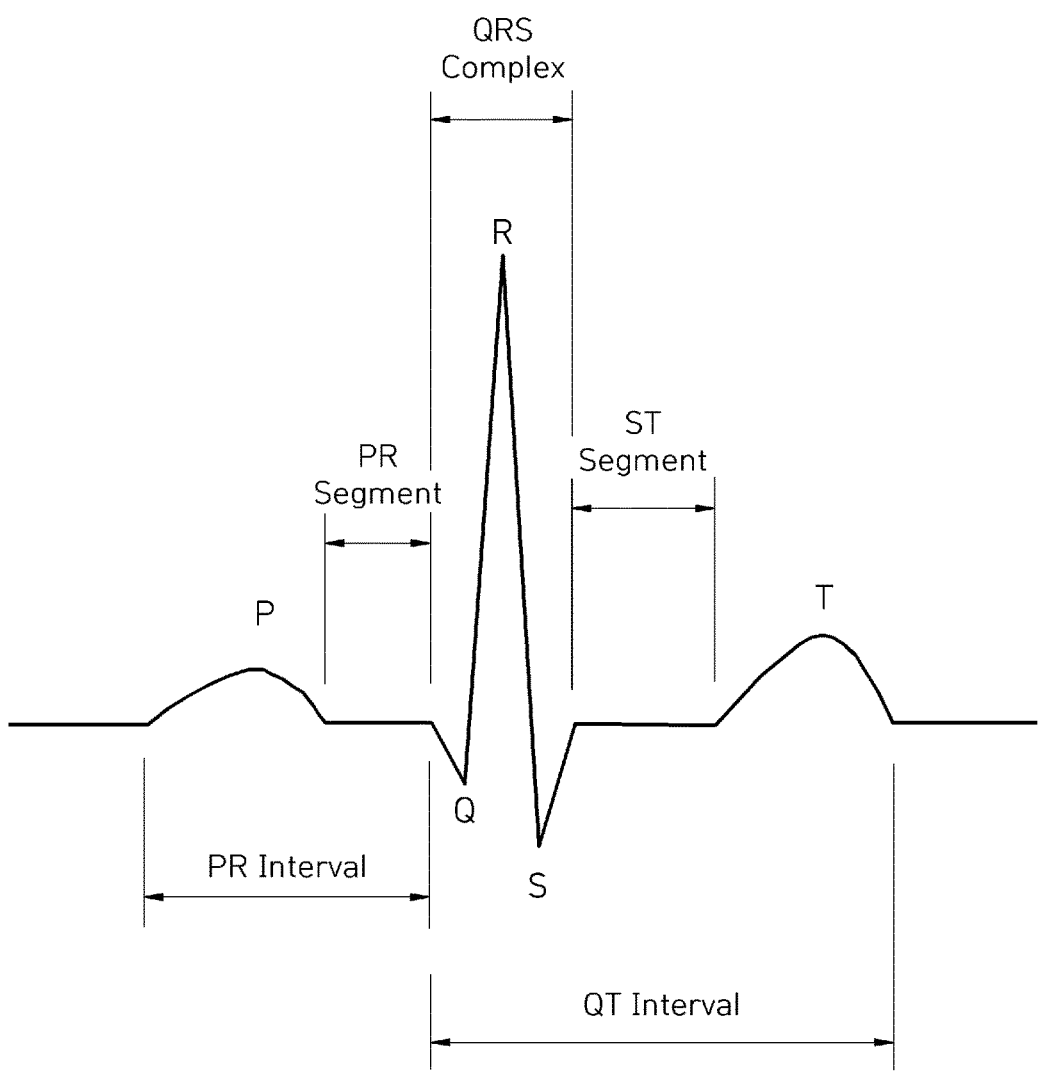
FIG. 1 is a diagram illustrating a waveform of a general electrocardiogram (ECG) signal.

Advantages and features of the present invention and methods for achieving them will be made clear from embodiments described in detail below with reference to the accompanying drawings. However, the present invention may be embodied in many different forms and should not be construed as being limited to the embodiments set forth herein. Rather, these embodiments are provided so that this disclosure will be thorough and complete and will fully convey the scope of the present invention to those of ordinary skill in the technical field to which the present invention pertains. The present invention is defined by the claims.

Meanwhile, terms used herein are for the purpose of describing the embodiments and are not intended to limit the present invention. In this specification, the singular forms include the plural forms unless the context clearly indicates otherwise. It will be understood that the terms "comprise" and/or "comprising," when used herein, specify some stated components but do not preclude the presence or addition of one or more other components. Throughout this specification, the same reference numerals refer to the same elements, and the term "and/or" includes any and all combinations of one or more referents. It will be understood that, although the terms "first," "second," etc. may be used herein to describe various elements, these elements should not be limited by these terms. These terms are only used to distinguish one element from another. Therefore, a first element described below may be a second element within the technological scope of the present invention.

Unless otherwise defined, all terms (including technical and scientific terms) used herein can be used as is customary in the art to which the present invention belongs. Also, it will be further understood that terms, such as those defined in commonly used dictionaries, will not be interpreted in an idealized or overly formal sense unless expressly so defined herein.

FIG. 1 is a diagram illustrating a waveform of a general electrocardiogram (ECG) signal.

The ECG is a graphical representation of electrical activity generated by the activity of the heart and, in this case, the electrical activity is obtained using electrodes placed on the skin. Such an ECG may include various waveforms.

First, an R peak is used as a reference point for detecting and dividing components of the ECG, and an interval between adjacent R peaks reflects heart rate information. However, obtained ECG signals not only have different aspects according to individual characteristics but also include abnormal signals and noise due to various types of diseases, and thus there is a need for a method of adaptively detecting R peaks for various ECG patterns.

Meanwhile, the components of the ECG are divided into P, Q, R, S, and T waves according to the order in which waveforms are generated. Since such a series of electrical waveforms coincide with a cardiac cycle, the ECG may be recorded so that a frequency of heartbeat and the electrical activity of the heart may be analyzed.

FIG. 1 illustrates a waveform of a general normal ECG signal and reflects typical shapes of the P, Q, R, S, and T waves. The P wave is generated during an atrial depolarization period, a group of the QRS waves reflects a ventricular depolarization period, and the T wave reflects a ventricular repolarization period.

A normal sinus P wave represents a normal atrial depolarization state, and the atrial depolarization starts near a sinoatrial node and is caused by conduction of electrical stimulation from right to left and downward across the atrium. A first part of the P wave represents depolarization of the right ventricle, and a rear part of the P wave represents depolarization of the left atrium. During a period of the P wave, an electric shock is transmitted from the sinoatrial node through atrial conduction and an atrioventricular node. The P wave is generated during a ventricular diastolic phase and rises suddenly or gradually from a base line. The P wave returns to the base line and is connected to a PR segment, a point where the PR segment starts becomes an end point of the P wave, a direction of the PR segment is a positive direction, and a duration of the PR segment is less than or equal to 0.1 seconds. The amplitude of the P wave ranges from 0.5 to 0.25 mm in induction and does not normally exceed about 2 mm on an ECG graph.

A QRS complex corresponds to depolarization of the ventricles and normally has a relationship of following each P wave. However, in cardiac arrhythmia such as atrioventricular block, the QRS complex does not follow each sinus P wave. Further, when the QRS complex is normal, a PR interval ranges from 0.12 to 0.2 seconds and, when the QRS complex is abnormal, the PR interval is less than or equal to 0.12 seconds or longer than 0.2 seconds. The normal QRS complex represents a state of depolarization of the normal ventricle, and the depolarization starts in a left part of an interventricular septum near an atrioventricular junction and proceeds from left to right across the interventricular septum. The Q wave, which is the beginning of the QRS complex, represents the depolarization of the interventricular septum, and a remaining part of the QRS complex represents the depolarization of the left and right ventricles that occur simultaneously. Since the left ventricle is larger than the right ventricle and has more muscles, most of the QRS complex exhibits the depolarization of the left ventricle.

The electric shock that causes the depolarization of the normal ventricle occurs in an upper part of the ventricle, such as the sinoatrial node, ectopic or deviant in the atrium, and atrioventricular junction, and then is conducted from below each of the right and left ventricles to the Purkinje tissue. The QRS complex starts to suddenly or gradually deviate from the base line and an end point thereof is a point flattened above or below the base line. An R peak of the QRS complex is a positive refraction that appears for the first time in the QRS complex and has the highest voltage compared to the other components of the ECG signal, and thus a rate of change over time is largest. The R peak not only determines a cycle of the ECG signal but also serves as a reference point for detecting and dividing the components of the ECG signal, and thus detection of the R peak is very important.

In the QRS complex, a Q wave is a first negative wave, which appears before an R wave, followed by the R peak, and is generated by the depolarization of the septum inside the atrium. Further, an S wave has a waveform in a shape of a negative refraction, which follows the R wave. The duration of the QRS complex ranges from 0.06 seconds to 0.1 seconds in adults and is about 0.08 seconds in children, and these results are obtained by measuring from a start point of the Q wave or R peak to an end point leading to the baseline.

Meanwhile, an RR interval is a period, in which the atrium and the ventricle each contract and relax once, and represents one cardiac circulation. The RR interval is an interval between peaks of the R peaks, and when the heartbeat is fast, the RR interval becomes narrower than that when the heartbeat is slow.

Finally, the T wave has a waveform that appears during the depolarization of the ventricle and is generated in two periods of an absolute refractory period and a relative refractory period. The T wave represents normal repolarization of the ventricle and proceeds starting from an epicardial surface of the ventricle toward an endocardial membrane through a ventricular wall. The T wave has a shape that shows a curve suddenly or gradually in an ST segment, and when there is no ST segment, the T wave starts at the end point of the QRS complex. When a point where the T wave returns to the base line becomes an end point of the T wave and when there is no ST segment, the T wave is called an ST-T wave. A direction of the T wave is a positive direction, and a duration of the T wave ranges from 0.1 seconds to 0.02 seconds or is longer than the range. The amplitude of the T wave is less than or equal to 5 mm, and a shape of the T wave is a sharp or blunt shape.

Hereinafter, a method (hereinafter, referred to as a method of detecting an R peak), which is performed by apparatuses 100 and 200 for detecting R peaks of ECG signals using an adaptive median filter, according to an embodiment of the present invention will be described with reference to FIGS. 2 to 8.

Figure 2:
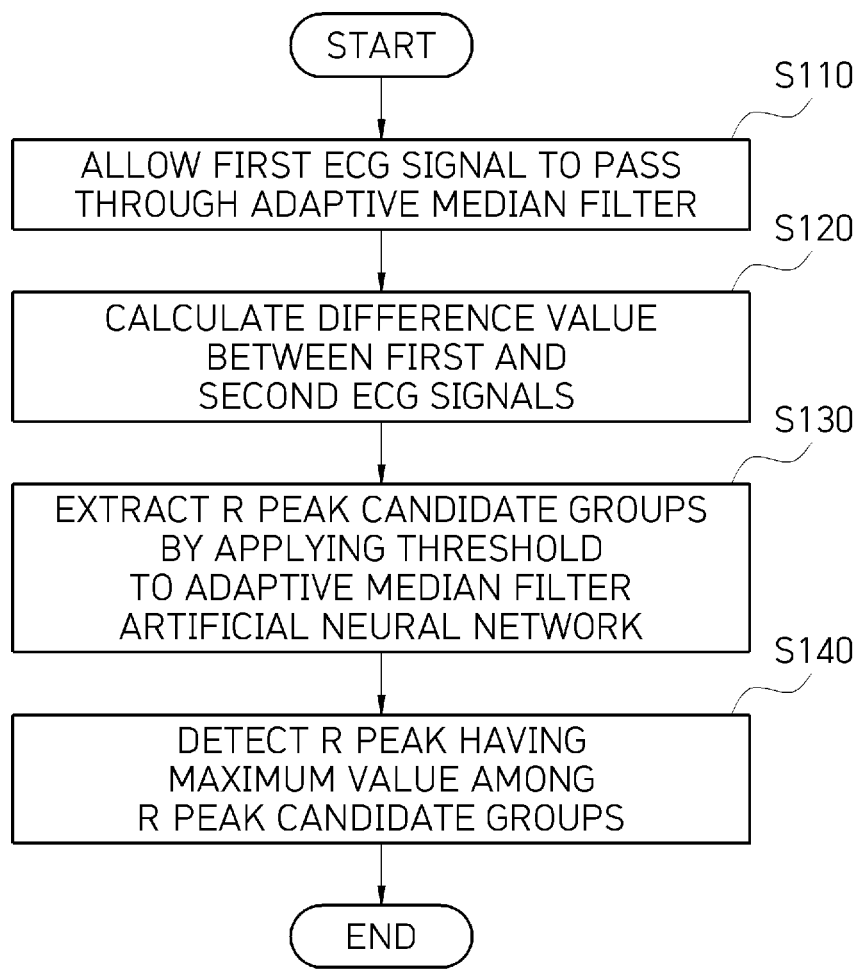
FIG. 2 is a flowchart for describing a method of detecting an R peak according to an embodiment of the present invention.

FIG. 2 is a flowchart for describing a method of detecting an R peak according to an embodiment of the present invention.

Meanwhile, operations illustrated in FIG. 2 may be understood as being performed by a server (hereinafter, referred to as a server) including the apparatuses 100 and 200 for detecting R peaks, but the present invention is not limited thereto.

First, the server allows an ECG signal (hereinafter, referred to as a first ECG signal) received from an ECG signal measuring apparatus having a predetermined sampling rate to pass through an adaptive median filter (S110). Then, the server calculates a difference value between the first ECG signal and a signal (hereinafter, referred to as a second ECG signal) passing through the adaptive median filter (S120).

Here, the sampling rate of the ECG signal measuring apparatus is not limited to a sampling rate of a specific value, and the ECG signal measuring apparatus may include a plurality of ECG signal measuring apparatuses having sampling rates of various values. That is, in the embodiment of the present invention, a filtering size is variable so that the adaptive median filter corresponds to the sampling rate of the ECG signal measuring apparatus, and thus any ECG signal measuring apparatus having various sampling rates may be used.

In the adaptive median filter according to the embodiment of the present invention, the filtering size in which the R peak is suppressed in the first ECG signal, in which the P wave and the T wave remain, is adaptively changed according to the sampling rate.

The adaptive median filter according to the embodiment of the present invention is shown in Equation 1.

$$M_{i,n} = \text{median}_{r \in W}(S_{i+r,a})$$ [Equation 1]

Here, S denotes the first ECG signal, and i denotes a location of an ECG sample point in an $n^{th}$ sliding window. Further, W denotes a filter window to which the adaptive median filter is applied.

The server may set a filtering size r of the adaptive median filter on the basis of a default size value L of a filter window, which is determined by a sampling rate Fs and to which a median filter is applied, and a size change value C of the filter window.

$$\begin{cases} r = L - C, & v_{min}(S_n) \leq v(S_{i,n}) < D_v(S_n)/3 \\ r = L, & D_v(S_n)/3 \leq v(S_{i,n}) < D_v(S_n) \times 2/3 \\ r = L + C, & D_v(S_n) \times 2/3 \leq v(S_{i,n}) \leq v_{max}(S_n) \end{cases}$$ [Equation 2]

where $L = Fs/60$, $C = Fs/(60 \times 2)$

Specifically, when a variance value $v(S_{i,n})$ of an $i^{th}$ sample point in the $n^{th}$ sliding window of the first ECG signal is greater than or equal to a minimum variance value $v_{min}(S_n)$ in the $n^{th}$ sliding window and is less than a value obtained by applying a first predetermined ratio (e.g., 1/3) to a difference value $D_v(S_n)$ between the minimum variance value $v_{min}(S_n)$ and a maximum variance value $v_{max}(S_n)$, the server may set a difference value (L−C) between the default size value L of the filter window and the size change value C of the filter window as the filtering size r.

In contrast, when the variance value $v(S_{i,n})$ of the $i^{th}$ sample point in the $n^{th}$ sliding window of the first ECG signal is greater than or equal to the value obtained by applying the first predetermined ratio (e.g., 1/3) to the difference value $D_v(S_n)$ between the minimum variance value $v_{min}(S_n)$ and the maximum variance value $v_{max}(S_n)$ in the $n^{th}$ sliding window of the median filter and is less than a value obtained by applying a second predetermined ratio (e.g., 2/3) greater than the first predetermined ratio to the difference value $D_v(S_n)$ between the minimum variance value $v_{min}(S_n)$ and the maximum variance value $v_{max}(S_n)$, the server may set the default size value L of the filter window as the filtering size.

Further, when the variance value $v(S_{i,n})$ of the $i^{th}$ sample point in the $n^{th}$ sliding window of the first ECG signal is greater than or equal to the value obtained by applying the second predetermined ratio greater than the first predetermined ratio to the difference value $D_v(S_n)$ between the minimum variance value $v_{min}(S_n)$ and the maximum variance value $v_{max}(S_n)$ and is less than or equal to the maximum variance value $v_{max}(S_n)$ in the $n^{th}$ sliding window, the server may set a sum value (L+C) of the default size value L of the filter window and the size change value C of the filter window as the filtering size r.

Figure 3B:
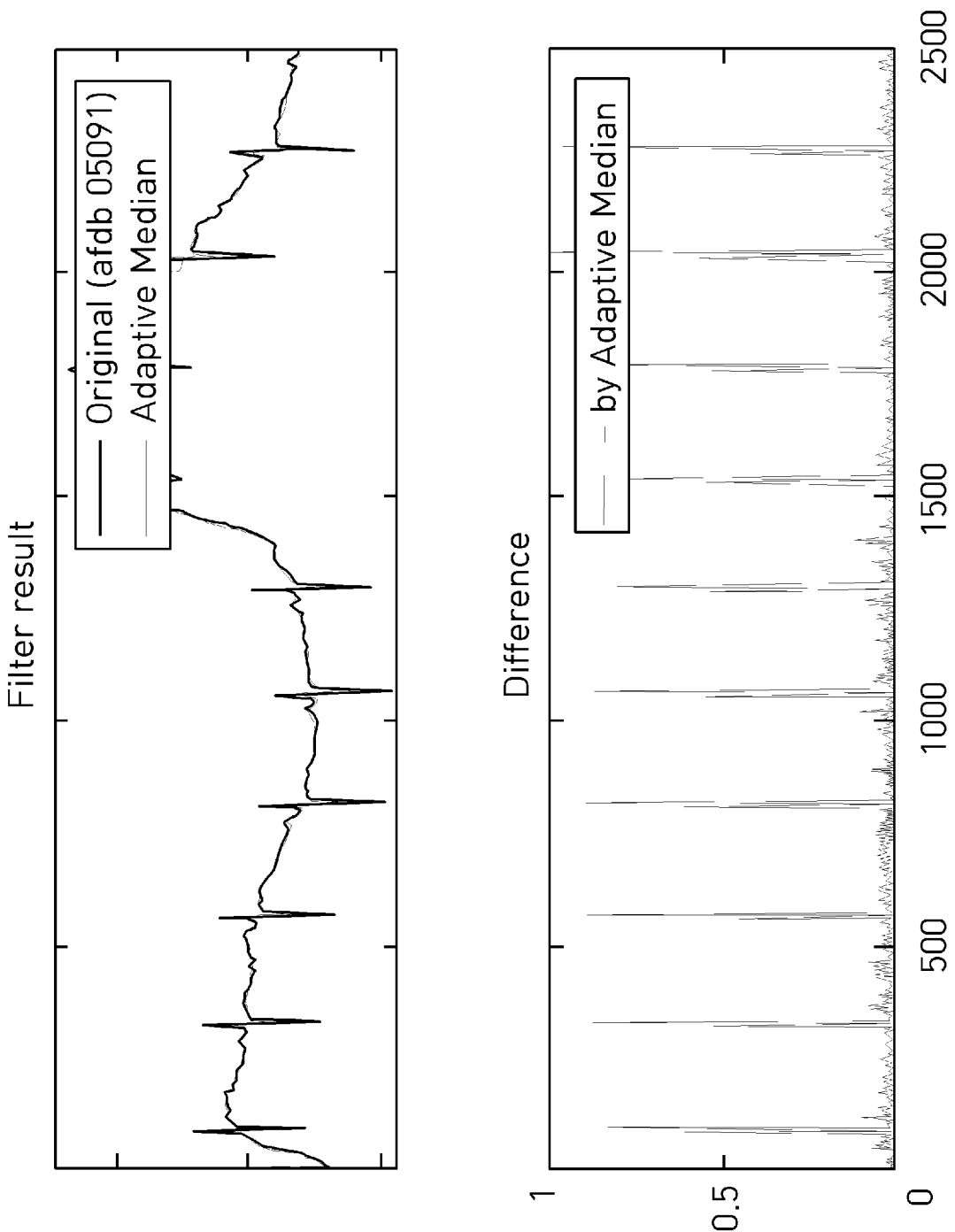

FIGS. 3A and 3B illustrate graphs showing filtering results and difference values of first ECG signals using a general median filter and an adaptive median filter according to the present invention.

Referring to FIGS. 3A and 3B, a second ECG signal is obtained by passing the first ECG signal through each of the general median filter and the adaptive median filter and then calculating a difference value between the first ECG signal and the second ECG signal. As a result of the calculating, it can be seen that, when the adaptive median filter proposed in the present invention is used, a difference value from the original signal is greater than that when the general median filter is used.

Referring again to FIG. 1, the server extracts R peak candidate groups by applying a maximum filtering size and an adaptive threshold applicable in the median filter to the calculated difference value between the first and second ECG signals (S130) and detects an R peak candidate group having a maximum value among the R peak candidate groups as an R peak (S140).

Figure 4:
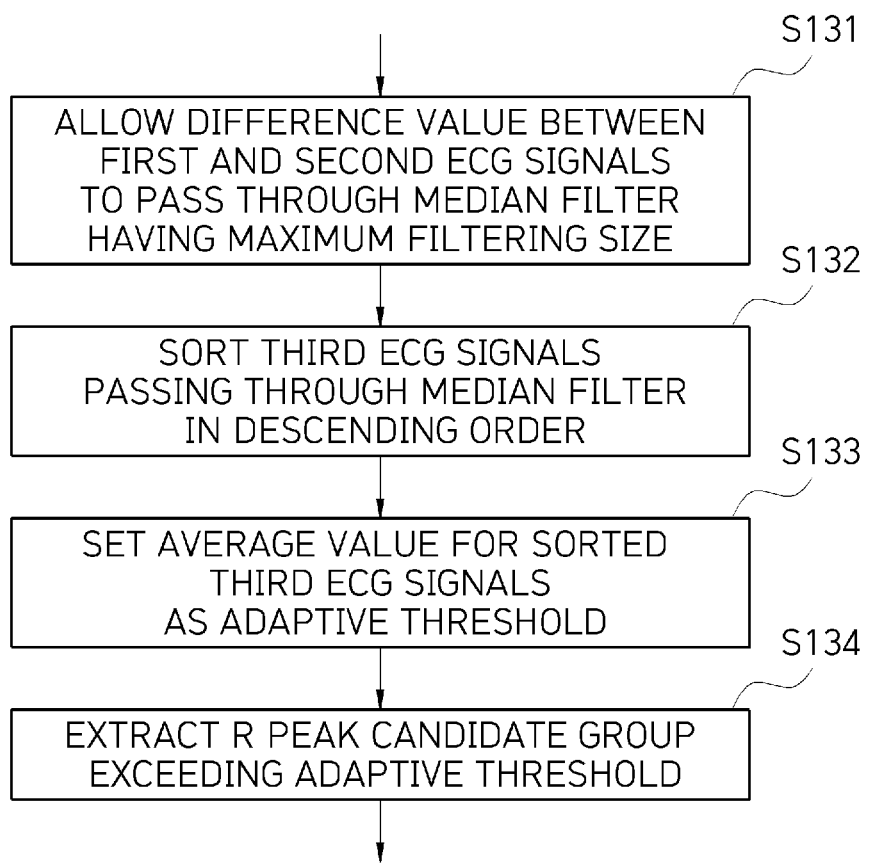
FIG. 4 is a flowchart for describing an operation of applying a maximum filtering size and an adaptive threshold.
Figure 5A:
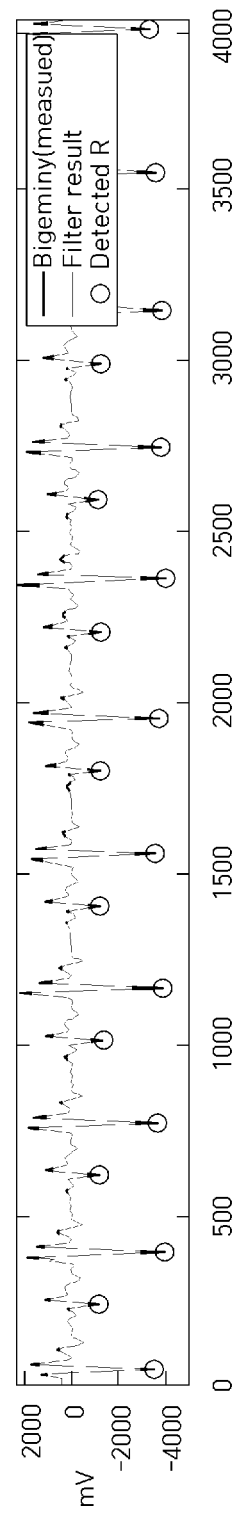
FIGS. 5A to 6C illustrate graphs showing adaptive thresholds in bigeminy and trigeminy, respectively.
Figure 5B:
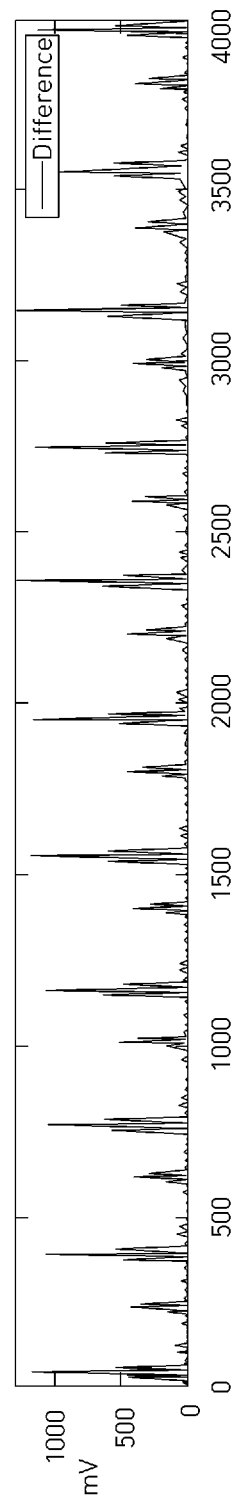
Figure 5C:
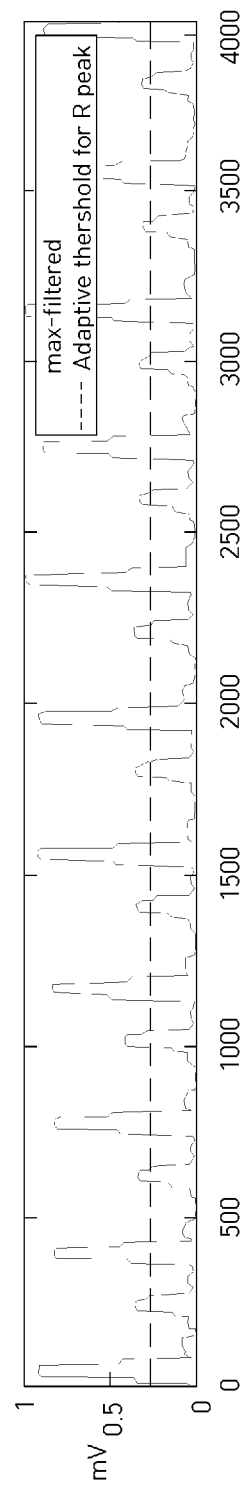
Figure 6A:
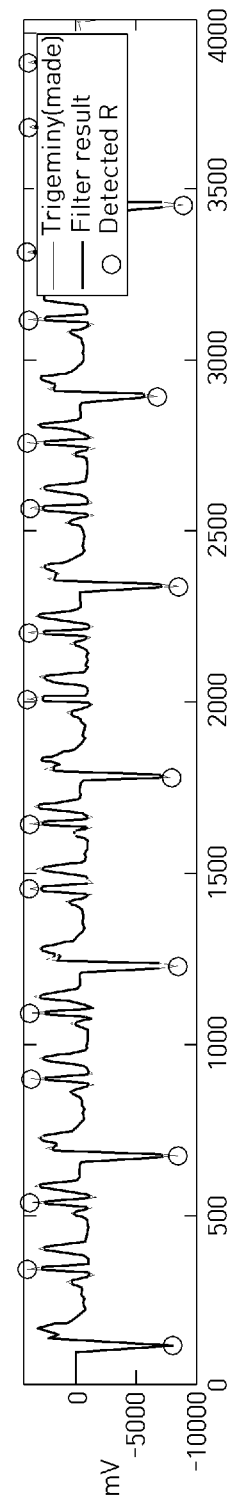
Figure 6B:
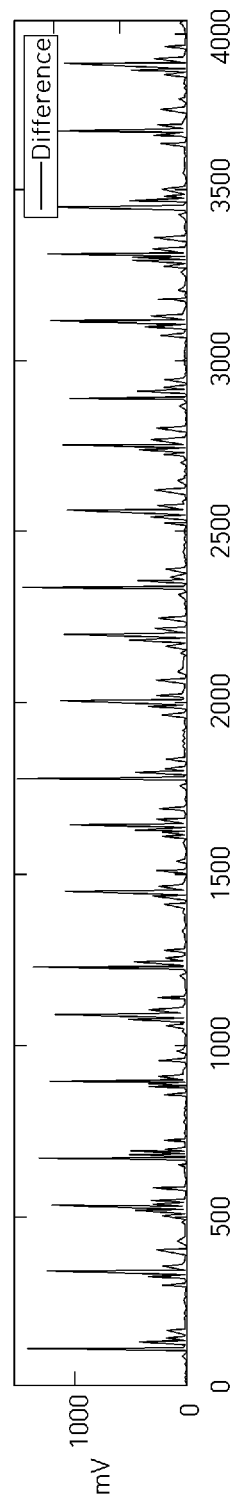
Figure 6C:
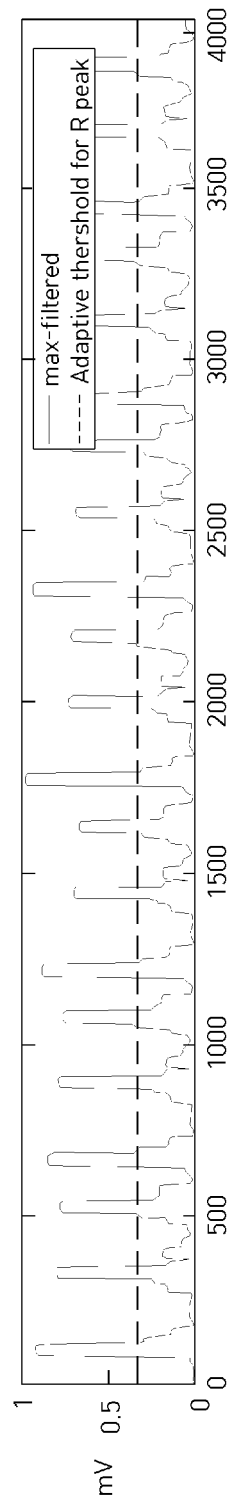
Figure 7A:
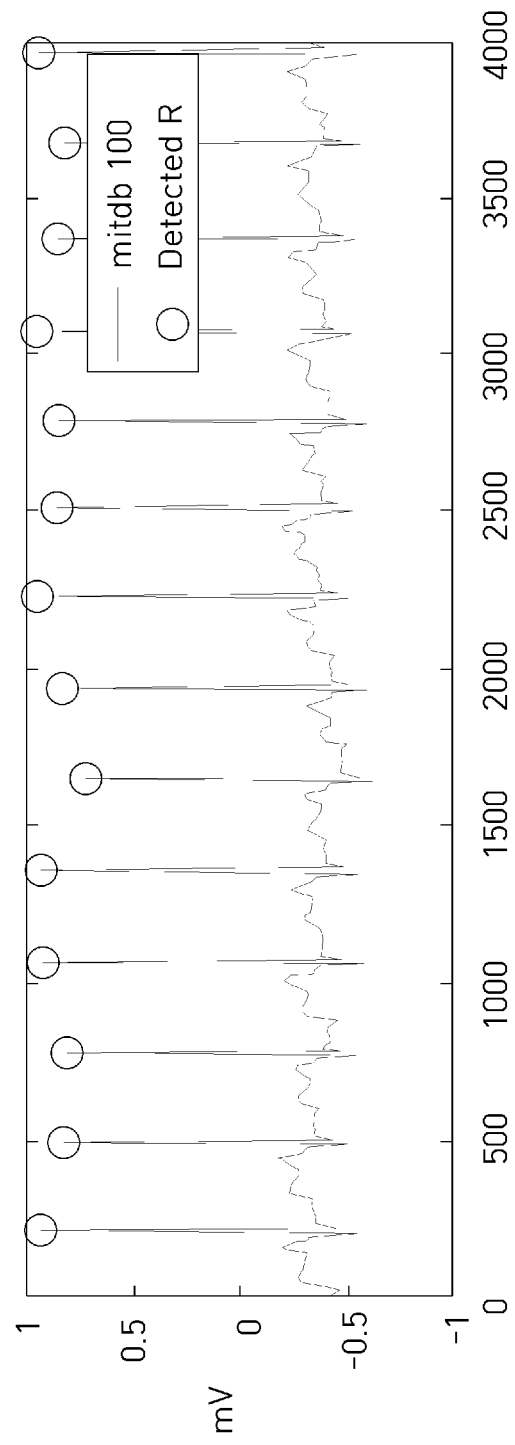
FIG. 7A to 7D illustrate graphs showing results of R peak detection in an MIT-BIH arrhythmia database (MITDB)
Figure 7B:
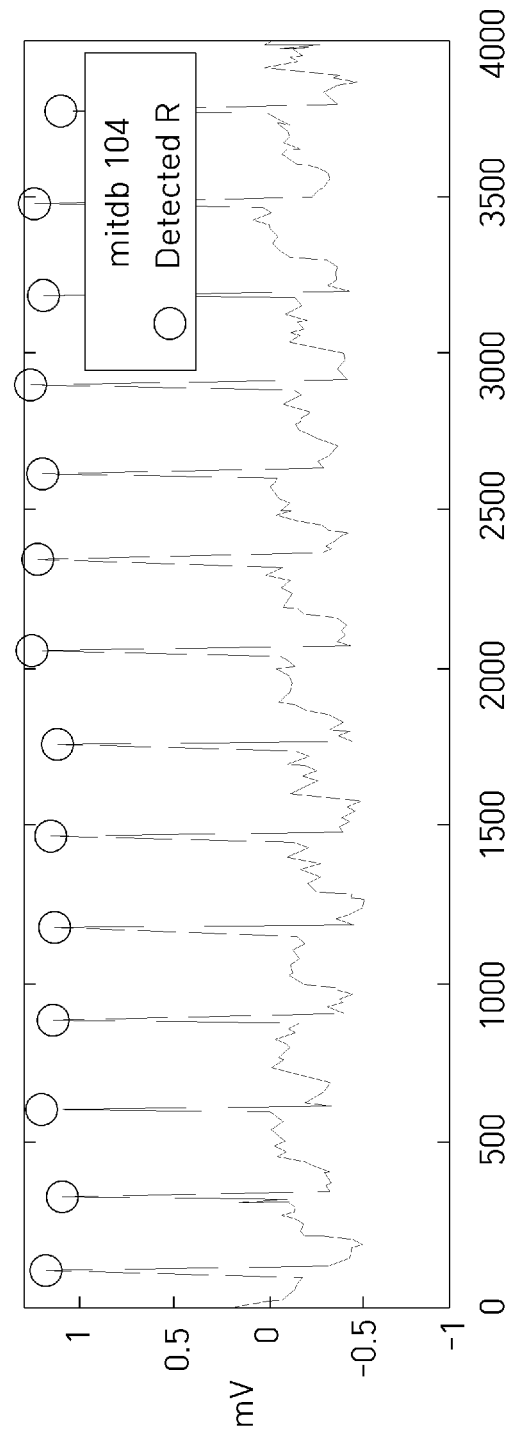
Figure 7C:
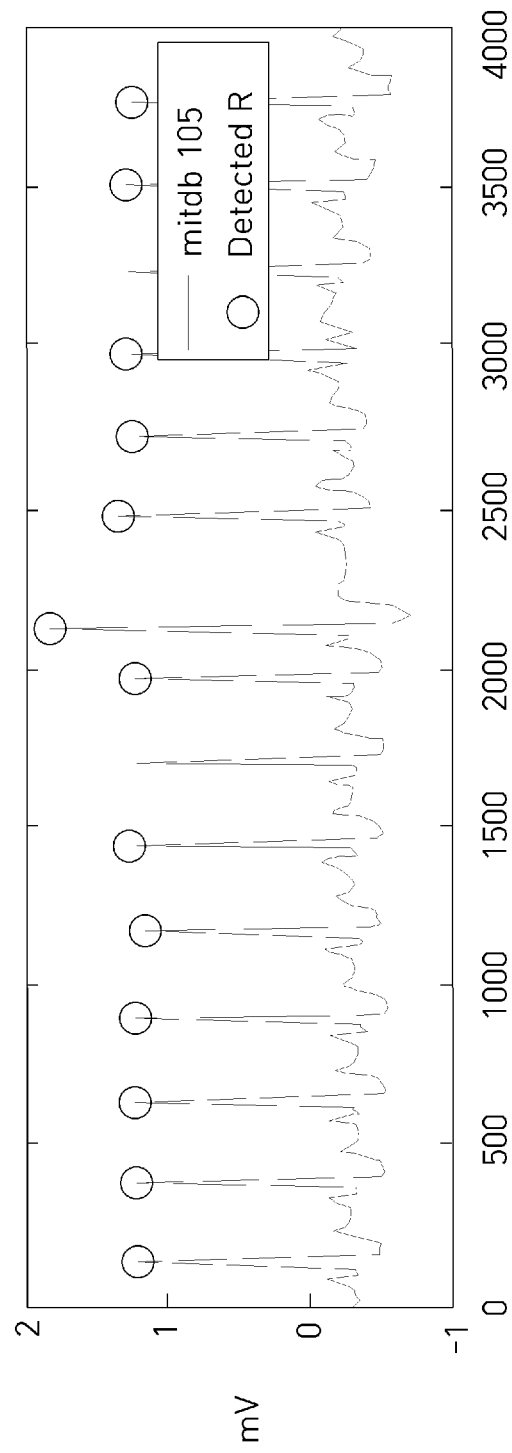
Figure 7D:
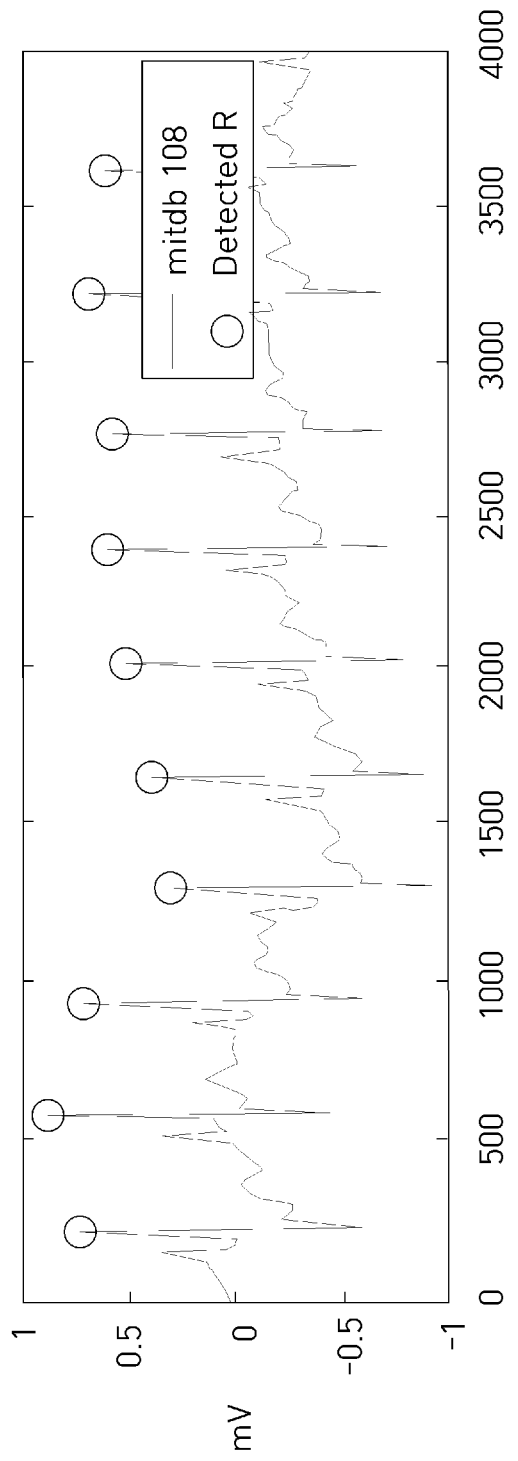

FIG. 4 is a flowchart for describing the operation of applying the maximum filtering size and the adaptive threshold. FIGS. 5A and 5B illustrate graphs showing adaptive thresholds in bigeminy and trigeminy.

In an embodiment, the server allows a signal having the calculated difference value between the first and second ECG signals to pass through a median filter having a maximum filtering size (S131). For example, the maximum filtering size may be set based on a sampling rate and may be set to Fs/8, but the present invention is not limited thereto.

Next, the server sorts signals (hereinafter, referred to as third ECG signals) passing through the median filter having the maximum filtering size in descending order (S132) and sets an average value for a predetermined top ratio of the third ECG signals sorted in descending order as an adaptive threshold (S133). In this case, the third ECG signals to which the maximum filtering size is applied as the adaptive threshold may be sorted in descending order and an average value of the third ECG signals of the top 70% may be used.

Next, the server extracts sections exceeding the adaptive threshold as the R peak candidate groups (S134).

Referring to FIGS. 5A to 6C, a result obtained by allowing signals having difference values shown in (FIG. 5B, 6B) between the first and second ECG signals to pass through the median filter having the maximum filtering size is shown in (FIG. 5C, 6C), and it can be seen that the thresholds in bigeminy and trigeminy are changed adaptively. In the case of the bigeminy, the adaptive threshold is calculated and applied as 0.2735, and in the case of the trigeminy, the adaptive threshold is calculated and applied as 0.3348. It can be seen that the threshold in the case of the bigeminy is lower than that in the case of the trigeminy, and results of the R peak detection are as shown in (FIG. 5A, 6A).

FIG. 7A to 7D illustrate graphs showing results of R peak detection in an MIT-BIH arrhythmia database (MITDB).

FIG. 7A to 7D shows results of R point detection for records 100, 104, 105, and 108 in the MITDB, and it can be seen that R points are easily detected for multiple signals.

FIG. 8 is a diagram illustrating an example of an R peak detection pseudo code applied to an embodiment of the present invention. FIG. 8 is a diagram illustrating an example of a structure of a sliding window.

In the pseudo code of FIG. 8, a sampling rate Fs is set as 250, a particle time Tp in the sliding window is set as 6 seconds, the number NSB of sliding windows for one minute is set as 3, the number N_Tp of particle times in the sliding window is set as 4, a step-size SS of the sliding window corresponding to the first ECG signal is set, and a time TS of the sliding window is set as Tp*N_Tp*Fs.

In this case, the step-size SS of the sliding window corresponding to the first ECG signal is automatically determined based on the particle time, the number of particle times, and the sampling rate, and is as shown in Equation 3.

$$SS = \text{round}(Tp*N\_Tp-1)*Fs \quad \text{[Equation 3]}$$

According to the pseudo code, in the embodiment of the present invention, the R peaks and other main features may be detected in units of sliding windows according to the sequentially entering first ECG signals.

That is, it is possible to detect a width of the QRS complex as well as the R peak through the sliding window and determine whether a current ECG is normal, whether a symptom of premature ventricular contraction (PVC) is present, or whether a symptom of ischemia or contraction is present.

Further, it is possible to calculate an atrial activity, an RR interval, a heart rate, a triangular index, an NN triangular interpolation of an NN histogram, standard deviation 1 (sd1), standard deviation 1 (sd2), an oscillation degree, and the like and determine whether the ECG signal per minute represents bigeminy, trigeminy, atrial fibrillation, ventricular tachycardia, supraventricular tachycardia, or the like based on the basis of the above calculated features.

Figure 9:
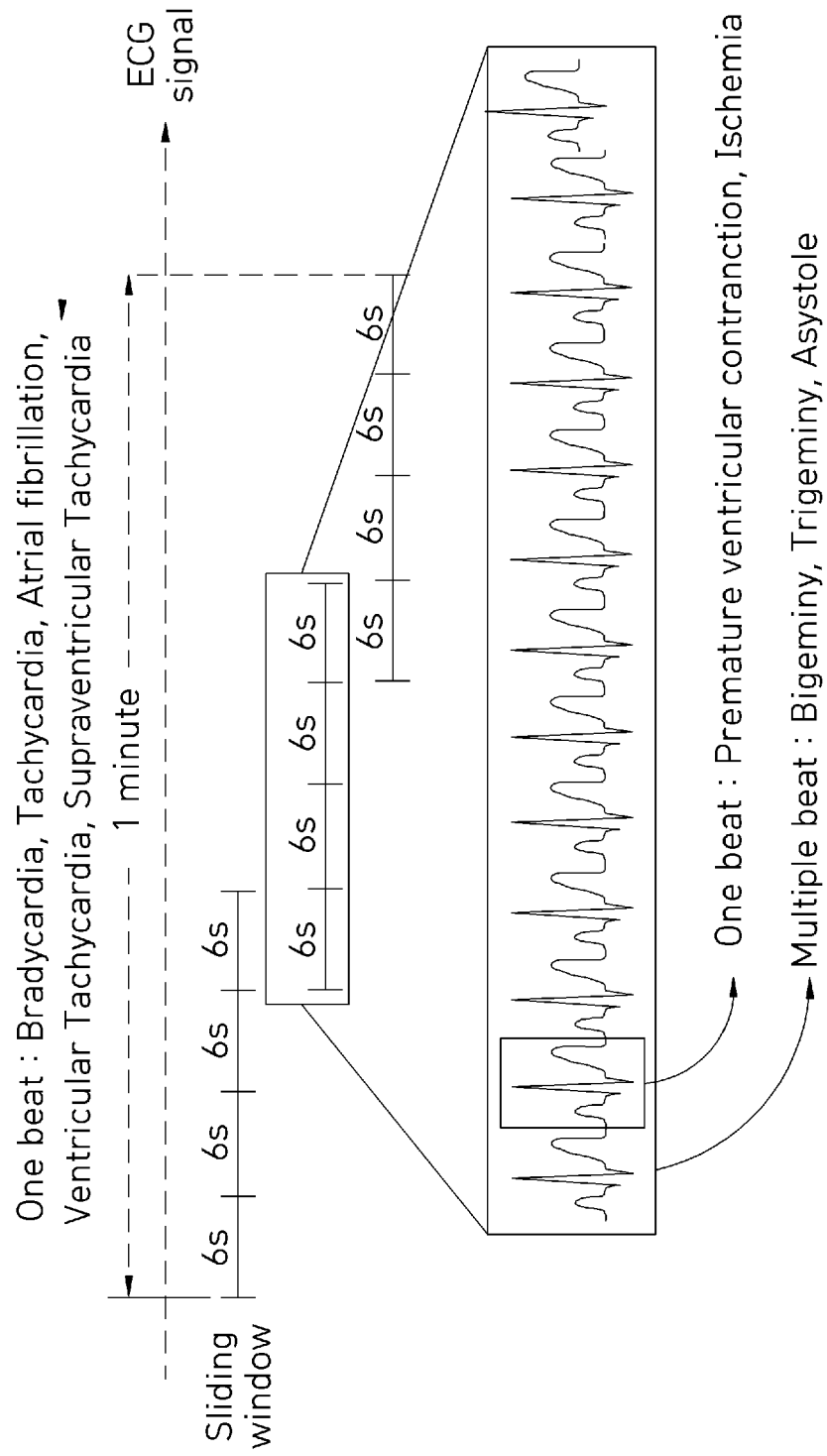
FIG. 9 is a diagram illustrating an example of a structure of a sliding window.

FIG. 9 shows a structure of a sliding window for detecting cardiac arrhythmia, and a particle time of the sliding window is set as 6 seconds. Therefore, the sliding window is set as 24 seconds, a step-size is set as 18 seconds, and an overlap time between the sliding windows is set as 6 seconds.

In the embodiment of the present invention, the detected R peaks for each sliding window set as described above may be connected in time series so that a result of the R peak detection may be provided.

Meanwhile, in the above description, operations S100 to S140 may be further divided into additional operations or may be combined into a fewer number of operations according to embodiments of the present invention. Further, some operations may be omitted as necessary or the order of the operations may be changed. In addition, even when contents are omitted, the contents described in FIGS. 2 to 8 are also applied to apparatuses 100 and 200 for detecting R peaks of FIGS. 9 and 10.

Hereinafter, the apparatuses 100 and 200 (hereinafter, referred to as R peak detection apparatuses) for detecting R peaks of ECG signals using an adaptive median filter according to embodiments of the present invention will be described.

Figure 10:
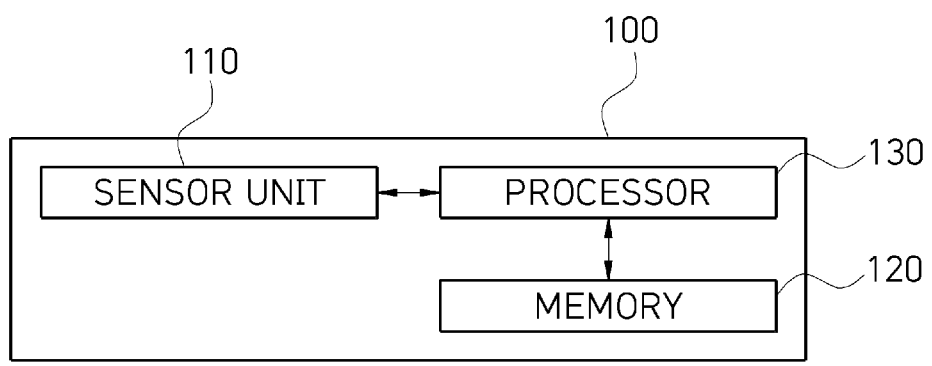
FIGS. 10 and 11 are diagrams for describing apparatuses for detecting R peaks according to embodiments of the present invention.
Figure 11:
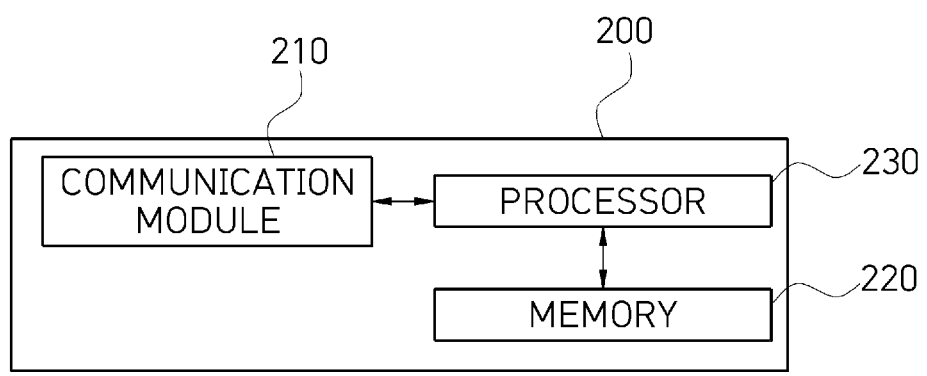

FIGS. 10 and 11 are diagrams for describing the R peak detection apparatuses 100 and 200 according to the embodiments of the present invention.

Referring to FIG. 10, the R peak detection apparatus 100 includes a sensor unit 110, a memory 120, and a processor 130.

The sensor unit 110 detects an ECG signal (hereinafter, referred to as a first ECG signal) having a predetermined sampling rate. In this case, the sampling rate of the sensor unit 110 is not limited to a specific value, and sensor units having various sampling rates may be applied.

A program for detecting an R peak from the first ECG signal using the adaptive median filter is stored in the memory 120, and the processor 130 executes the program stored in the memory 120.

The processor 130 calculates a difference value between the first ECG signal and a signal (hereinafter, referred to as a second ECG signal) obtained by allowing the first ECG signal to pass through the adaptive median filter, extracts R peak candidate groups by applying a maximum filtering size and an adaptive threshold applicable in the median filter to the calculated difference value between the first and second ECG signals, and detects an R peak candidate group having a maximum value among the R peak candidate groups as an R peak.

In another embodiment, the R peak detection apparatus 200 is configured separately from a sensor unit, and the sensor unit may be provided in a separate ECG signal measuring apparatus. Accordingly, the R peak detection apparatus 200 receives a measured ECG signal from an ECG signal measuring apparatus having a predetermined sampling rate through a communication module 210.

The method of detecting the R peak of the ECG signal using the adaptive median filter according to the embodiment of the present invention described above may be implemented as a program (or an application) to be executed in combination with the server, which is hardware, and may be stored in a medium.

In order for a computer to read the program and execute the above methods implemented as programs, the above-described program may include code coded in a computer language such as C, C++, JAVA, or machine language that may be read by a processor (a central processing unit (CPU)) of the computer through a device interface of the computer. The code may include functional code related to functions that define necessary functions for executing the methods, and the like and include control code related to an execution procedure necessary for the processor of the computer to execute the functions according to a predetermined procedure. Further, the code may further include additional information required for the processor of the computer to execute the functions, or code related to memory reference to which a location (address) of an internal or external memory of the computer should be referenced. Further, when the processor of the computer needs to communicate with any other computer or server at a remote location in order to execute the functions, the code may further include code related to communication for how to communicate with any other computers or servers at remote locations using a communication module of the computer and for what information or media should be transmitted and received during communication.

The storage medium is not a medium in which data is stored for a short moment, such as a register, a cache, a memory, etc., but refers to a medium in which data is stored semi-permanently and is readable by a device. Specifically, examples of the storage medium include a read only memory (ROM), a random access memory (RAM), a compact disc ROM (CD-ROM), a magnetic tape, a floppy disk, an optical data storage device, and the like, but the present invention is not limited thereto. That is, the program may be stored in various recording media on various servers to which the computer may access or may be stored in various recording media of the user's computer. Further, the media may be distributed over computer systems connected through a network, and computer-readable code may be stored in a distributed manner.

The operations of the method or algorithm described in connection with the embodiments of the present invention may be implemented directly in hardware, implemented as a software module executed by hardware, or implemented by a combination thereof. The software module may reside in a RAM, a ROM, an erasable programmable ROM (EPROM), an electrically erasable programmable ROM (EEPROM), a flash memory, a hard disk, a removable disk, a CD-ROM, or any type of computer-readable recording medium well known in the art.

According to the present invention as described above, by adaptively changing a filtering size according to a sampling rate of an ECG measuring apparatus, changing an amount of change in filtering size on the basis of a variance value of a sample point, and adaptively changing a threshold value of an R peak, the above changed features can be directly applied to the ECG signal measured from the ECG measuring apparatus having various sampling rates.

Effects of the present invention are not limited to the above-described effects and other unmentioned effects may be clearly understood by those skilled in the art from the above descriptions.

Although the embodiments of the present invention have been described with reference to the accompanying drawings, it will be understood by those skilled in the art that various modifications can be made without departing from the technical scope of the present invention and without changing essential features. Therefore, the above-described embodiments should be considered in a descriptive sense only and not for purposes of limitation.

What is claimed is:

1. A method of detecting an R peak of an electrocardiogram (ECG) signal using an adaptive median filter, which is performed by a computer, the method comprising:
    allowing an ECG signal (hereinafter, referred to as a first ECG signal) received from an ECG signal measuring apparatus having a predetermined sampling rate to pass through an adaptive median filter;
    calculating a difference value between the first ECG signal and a signal (hereinafter, referred to as a second ECG signal) passing through the adaptive median filter;
    extracting R peak candidate groups by applying a maximum filtering size and an adaptive threshold applicable in the adaptive median filter to the calculated difference value between the first and second ECG signals; and
    detecting an R peak candidate group having a maximum value among the R peak candidate groups as an R peak.

2. The method of claim 1, wherein the adaptive median filter has a filtering size set to correspond to the sampling rate.

3. The method of claim 1, further comprising setting a filtering size of the adaptive median filter on the basis of a default size value of a filter window, which is determined by the sampling rate and to which the adaptive median filter is applied, and a size change value of the filter window.

4. The method of claim 3, wherein the setting of the filtering size of the adaptive median filter includes setting a difference value between the default size value of the filter window and the size change value of the filter window as the filtering size when a variance value of an $i^{th}$ (i is a nature number) sample point in an $n^{th}$ (n is a nature number) sliding window of the first ECG signal is greater than or equal to a minimum variance value in the $n^{th}$ sliding window and is less than a value obtained by applying a first predetermined ratio to a difference value between the minimum variance value and a maximum variance value.

5. The method of claim 3, wherein the setting of the filtering size of the adaptive median filter includes setting the default size value of the filter window as the filtering size when a variance value of an $i^{th}$ (i is a nature number) sample point in an $n^{th}$ (n is a nature number) sliding window of the first ECG signal is greater than or equal to a value obtained by applying a first predetermined ratio to a difference value between a minimum variance value and a maximum variance value in an $n^{th}$ sliding window of the adaptive median filter and is less than a value obtained by applying a second predetermined ratio greater than the first predetermined ratio to the difference value between the minimum variance value and the maximum variance value.

6. The method of claim 3, wherein the setting of the filtering size of the adaptive median filter includes setting a sum value of the default size value of the filter window and the size change value of the filter window as the filtering size when a variance value of an $i^{th}$ (i is a nature number) sample point in an $n^{th}$ (n is a nature number) sliding window of the first ECG signal is greater than or equal to a value obtained by applying a second predetermined ratio greater than the first predetermined ratio to a difference value between a minimum variance value and a maximum variance value and is less than or equal to the maximum variance value in the $n^{th}$ sliding window.

7. The method of claim 1, wherein a step-size of a sliding window corresponding to the first ECG signal is automatically set based on particle times, the number of the particle times, and the sampling rate.

8. The method of claim 7, wherein the detecting of the R peak candidate group having the maximum value among the R peak candidate groups as the R peak includes connecting the R peaks for each sliding window set in time series and providing the connected R peaks.

9. The method of claim 1, wherein the extracting of the R peak candidate group by applying the maximum filtering size and the adaptive threshold applicable in the adaptive median filter to the calculated difference value between the first and second ECG signals includes:
   allowing a signal having the calculated difference value between the first and second ECG signals to pass through a median filter having a maximum filtering size;
   sorting signals (hereinafter, referred to as third ECG signals) passing through the median filter having the maximum filtering size in descending order;
   setting an average value for a predetermined top ratio of the third ECG signals sorted in descending order as the adaptive threshold; and
   extracting sections exceeding the adaptive threshold as the R peak candidate groups.

10. An apparatus for an R peak of an electrocardiogram (ECG) signal using an adaptive median filter, the apparatus comprising:
   a sensor unit configured to detect an ECG signal (hereinafter, referred to as a first ECG signal) having a predetermined sampling rate;
   a memory configured to store a program for detecting an R peak from the first ECG signal using the adaptive median filter; and
   a processor configured to execute the program stored in the memory,
   wherein the processor executes the program to calculate a difference value between the first ECG signal and a signal (hereinafter, referred to as a second ECG signal) obtained by allowing the first ECG signal to pass through the adaptive median filter, extract R peak candidate groups by applying a maximum filtering size and an adaptive threshold applicable in the adaptive median filter to the calculated difference value between the first and second ECG signals, and detect an R peak candidate group having a maximum value among the R peak candidate groups as an R peak.

11. An apparatus for an R peak of an electrocardiogram (ECG) signal using an adaptive median filter, the apparatus comprising:
   a communication module configured to receive a measured ECG signal (hereinafter, referred to as a first ECG signal) from an ECG signal measuring apparatus having a predetermined sampling rate;
   a memory configured to store a program for detecting an R peak from the first ECG signal using the adaptive median filter so that a filtering size is set to correspond to the sampling rate; and
   a processor configured to execute the program stored in the memory,
   wherein the processor executes the program to calculate a difference value between the first ECG signal and a signal (hereinafter, referred to as a second ECG signal) obtained by allowing the first ECG signal to pass through the adaptive median filter, extract R peak candidate groups by applying a maximum filtering size and an adaptive threshold applicable in the adaptive median filter to the calculated difference value between the first and second ECG signals, and detect an R peak candidate group having a maximum value among the R peak candidate groups as an R peak.

12. The apparatus of claim 11, wherein the processor sets the filtering size of the adaptive median filter on the basis of a default size value of a filter window to which the adaptive median filter determined by the sampling rate is applied and a size change value of the filter window.

13. The apparatus of claim 12, wherein the processor sets a difference value between the default size value of the filter window and the size change value of the filter window as the filtering size when a variance value of an $i^{th}$ (i is a nature number) sample point in an $n^{th}$ (n is a nature number) sliding window of the first ECG signal is greater than or equal to a minimum variance value in the $n^{th}$ sliding window and is less than a value obtained by applying a first predetermined ratio to a difference value between the minimum variance value and a maximum variance value.

14. The apparatus of claim 12, wherein the processor sets the default size value of the filter window as the filtering size when a variance value of an $i^{th}$ (i is a nature number) sample point in an $n^{th}$ (n is a nature number) sliding window of the first ECG signal is greater than or equal to a value obtained by applying a first predetermined ratio to a difference value between a minimum variance value and a maximum variance value in the $n^{th}$ sliding window of the adaptive median filter and is less than a value obtained by applying a second predetermined ratio greater than the first predetermined ratio to the difference value between the minimum variance value and the maximum variance value.

15. The apparatus of claim 12, wherein the processor sets a sum value of the default size value of the filter window and the size change value of the filter window as the filtering size when a variance value of an $i^{th}$ (i is a nature number) sample point in an $n^{th}$ (n if a nature number) sliding window of the first ECG signal is greater than or equal to a value obtained by applying a second predetermined ratio greater than the first predetermined ratio to a difference value between a minimum variance value and a maximum variance value and is less than or equal to the maximum variance value in the $n^{th}$ sliding window.

16. The apparatus of claim 11, wherein a step-size of a sliding window corresponding to the first ECG signal is automatically set based on particle times, the number of the particle times, and the sampling rate.

17. The apparatus of claim 16, wherein the processor connects the R peaks for each sliding window set in time series to provide the connected R peaks.

18. The apparatus of claim 11, wherein the processor sorts signals (hereinafter, referred to as third ECG signals) obtained by allowing a signal having the calculated difference value between the first and second ECG signals to pass through a median filter having a maximum filtering size in descending order, and sets an average value for a predetermined top ratio of the third ECG signals sorted in descending order as the adaptive threshold, and then extracts sections exceeding the adaptive threshold as the R peak candidate group.

* * * * *